(12) United States Patent
Barrot

(10) Patent No.: US 10,674,733 B2
(45) Date of Patent: Jun. 9, 2020

(54) RESISTANCE TO HETERODERA CAROTAE AND METHODS FOR USE

(71) Applicant: VILMORIN & CIE, Paris (FR)

(72) Inventor: Laure Barrot, La Menitre (FR)

(73) Assignee: VILMORIN & CIE, Paris (FR)

( * ) Notice: Subject to any disclaimer, the term of this patent is extended or adjusted under 35 U.S.C. 154(b) by 40 days.

(21) Appl. No.: 15/566,559

(22) PCT Filed: Apr. 15, 2016

(86) PCT No.: PCT/EP2016/058304
§ 371 (c)(1),
(2) Date: Oct. 13, 2017

(87) PCT Pub. No.: WO2016/166262
PCT Pub. Date: Oct. 20, 2016

(65) Prior Publication Data
US 2018/0103647 A1    Apr. 19, 2018

(30) Foreign Application Priority Data
Apr. 17, 2015  (FR) .................................. 15 53449

(51) Int. Cl.
*A01N 65/10* (2009.01)
*A01N 25/00* (2006.01)
*C12N 15/82* (2006.01)

(52) U.S. Cl.
CPC ............. *A01N 65/10* (2013.01); *A01N 25/00* (2013.01); *C12N 15/8285* (2013.01)

(58) Field of Classification Search
CPC ...................................................... A01H 65/10
USPC .......................................................... 800/302
See application file for complete search history.

(56) References Cited

U.S. PATENT DOCUMENTS 4,442,092 A    4/1984  McBrayer

FOREIGN PATENT DOCUMENTS

WO    WO 2005/063989 A1    7/2005

OTHER PUBLICATIONS

Ali et al. (2013, J. of Heredity 105:288-291).*
International Search Report dated Jun. 24, 2016 in connection with PCT International Application No. PCT/EP2016/058304.

* cited by examiner

*Primary Examiner* — Li Zheng
(74) *Attorney, Agent, or Firm* — John P. White; Gary J. Gershik; Cooper & Dunham LLC

(57) ABSTRACT

The present application relates to the use of *Daucus carota* plants which do not belong to the *Daucus carota* subsp. *sativus* subspecies of cultured carrots to disinfect a culture medium infested with *Heterodera carotae* nematodes, using the nematicidal power of the plants. The present application also relates to *Daucus carota* plants which are resistant to the *Heterodera carotae* nematode, and to methods for culturing such plants which make it possible to reduce the population of *Heterodera carotae* nematodes present in a culture medium.

Figure 1:
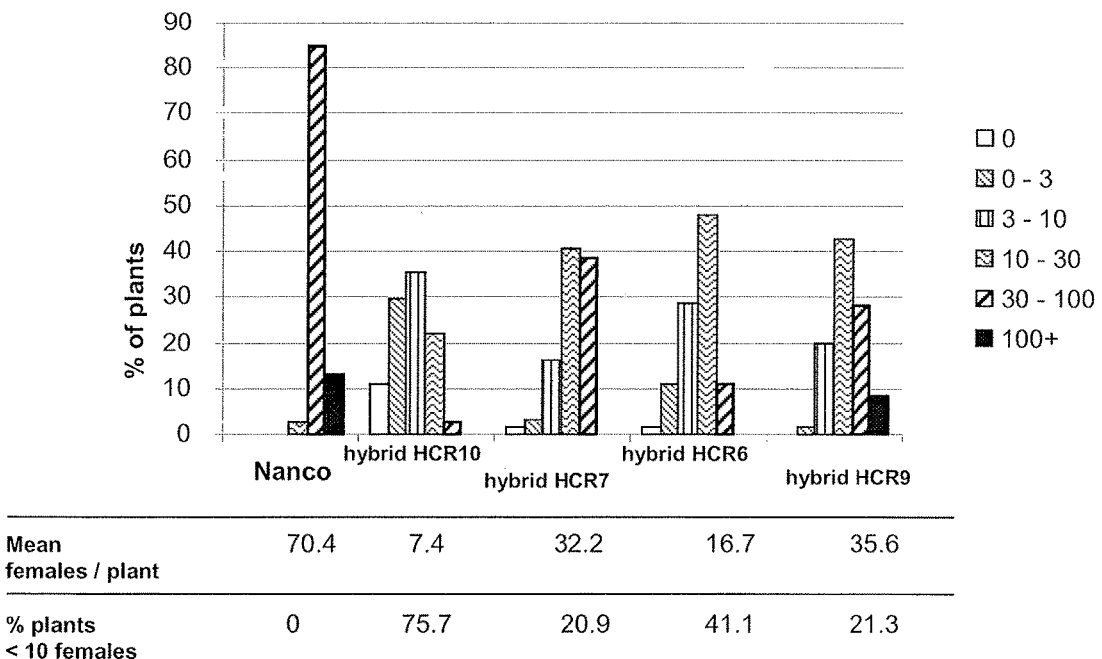

15 Claims, 3 Drawing Sheets ent is approximately 600000 tonnes, a large part of which, 350000 tonnes, being destined for the fresh market (fresh and processed), the rest being allocated to the production of carrots intended for industry.
RESISTANCE TO HETERODERA CAROTAE AND METHODS FOR USE

CROSS-REFERENCE TO RELATED APPLICATIONS

This application is a § 371 national stage of PCT International Application No. PCT/EP2016/058304, filed Apr. 15, 2016, claiming priority of French Patent Application No. FR 1553449, filed Apr. 17, 2015, the contents of each of which are hereby incorporated by reference into the application.

The present invention relates to a plant from the family *Daucus carota* with a nematicidal activity against the carrot cyst nematode *Heterodera carotae*, preferably not belonging to the cultivated carrot subspecies *Daucus carota* subsp. *sativus*. The present invention also relates to the uses of such a nematicidal *Daucus carota* plant, in particular to reduce the level of infestation of a crop field infested with the carrot cyst nematode *Heterodera carotae*.

Carrots belong to the apiaceae family, formerly known by the name umbelliferae. This biannual herbaceous plant is cultivated for its fleshy, edible root which is itself known as the carrot.

In accordance with the statistics of the Food and Agricultural Organization of the United Nations (FAO), in 2007, the global production of carrots was more than 26 million tonnes, with half of this coming from three countries—China, the United States and Russia.

Production in France is approximately 600000 tonnes, a large part of which, 350000 tonnes, being destined for the fresh market (fresh and processed), the rest being allocated to the production of carrots intended for industry.

While carrot production covers the whole of French territory, it is especially concentrated into four major zones, Western France (Normandy and Brittany), Aquitaine (Landes), the Mediterranean and the North Picardy region. The first two zones are particularly favourable primarily because of their sandy soil which is good for a balanced development of the roots and assists mechanization of the harvest.

On its own, French production intended for the fresh market represents a'surface area of more than 8500 hectares.

Carrots are a field crop; cultivating them has to meet many challenges. Phytosanitary protection of the carrot crop is of major interest to producers. The principal difficulties as regards disease and soil-dwelling pests are nematodes, pythiums, *Rhizoctonia solani* and the carrot fly (*Psila rosae*), and as regards airborne pests, the aphid *cavalriella aegopodii* and *Alternaria dauci*.

The carrot cyst nematode *Heterodera carotae* is responsible for high crop losses linked either to slowing down production or to a reduction in the size of the root combined with a high production of lateral rootlets which produces a fairly characteristic, hairy appearance but greatly devalues the product which can no longer be sold. In sandy terrains, production zones, losses linked to *Heterodera carotae* may be close to 90%.

Chemical control methods are currently the most effective methods for disinfecting fields. Thus, 1,3-dichloropropene brings about reductions in the nematode population in treated soils by an average of 80%. However, in a context in which the cultivation conditions have to comply more and more with environmental issues, these fumigating chemical treatments and/or nematicidal treatments in the case of nematodes raise environmental problems and their use is decreasing: 1,3-dichloropropene has recently been banned in Europe, leaving agriculturalists with no effective chemical control solutions for forthcoming planting seasons.

Furthermore, it has been observed that, while such chemical treatments can allow the carrot to be cultivated in an infested terrain, they do not bring about any stable reduction in nematode populations. In fact, after a treatment, there are still sufficient individuals, principally in the form of a cyst, to generate a new infesting population as soon as cultivation starts afresh. Thus, it is necessary to continuously renew these chemical treatments, which is expensive and also causes environmental issues.

A variety of other protective means are available, for example disinfecting the soils with steam or solar irradiation. However, the reductions in the nematode populations of 50% which have been observed mean that those methods are not optimal and they frequently turn out to be difficult to implement.

Crop rotation is a possibility which may be envisaged to combat certain pathogens, but it is not well suited in the case of carrot cyst nematodes which, in the absence of carrots, have the ability to stay in the soil in a suspended state for several years in the form of a cyst which hatches as soon as a new crop of carrots is sown and following the emission of root exudates. At least eight years without cultivating carrots on an infested plot is considered to be necessary before an acceptable threshold is reached for a new crop which will itself trigger an infestation for subsequent years.

Cultivation methods such as the carrot trap technique can be used to reduce the populations of nematodes in infected fields. The root exudates from carrots planted in the fields the nematode population of which is to be reduced will allow larvae to hatch. These latter will migrate into the roots, and mechanical destruction of the crop before the end of a complete cultivation cycle can stop the larvae from developing. This cultivation technique, however, suffers from limitations because not all of the cysts infecting a field hatch at the same time. If the crop is destroyed too soon, sufficient numbers of cysts remain in the field and bring about losses in the following crop. If the crop is destroyed too late, new larvae, or even new cysts are produced, which again will bring about production losses which follow use of the trap. Thus, it is extremely difficult to determine the optimal time at which the crop should be destroyed, and even when destruction is carried out at that time, because not all of the cysts hatch at the same time, it is almost impossible to obtain a degree of disinfection which is similar to that obtained with chemical products.

Of the varieties of carrot which are resistant to carrot cyst nematode, *Heterodera carotae* could provide an interesting solution, but currently, and despite huge research efforts in this regard, such varieties do not exist.

Thus, there is no effective non-chemical method for controlling the carrot cyst nematode *Heterodera carotae*. The present inventors have successfully developed an original technique using nematicidal *Daucus carota* plants which can sufficiently reduce the level of infestation of a crop field by the carrot cyst nematode *Heterodera carotae* in order to allow the cultivation of carrots.

The nematode class comprises more than 15000 species which are found in the soil and bodies of water; some of them have adopted a particular lifestyle, that of parasitism, dependent upon animals or plants.

The species *Heterodera carotae* was identified by Jones in 1950 in England and has since been found in the majority of European states where it causes large losses in production. It is a sedentary endoparasite which develops inside the plant tissue of the carrot. In the field, symptoms are zones of irregular vegetation, loss of vitality of foliage, colour changing to yellowish-brown with necrotic regions. The plants are not very vigorous. The root size is reduced, along with an intense production of rootlets which give the root a hairy appearance. Lignification occurs more rapidly and growth is irregular, which causes distortions and deformation of the taproot. The apex necrotizes. Nematode attack causes a high water stress in the plant; yield losses could possibly be limited by irrigating the crop and by supplying fertilizer.

The life cycle of the carrot cyst nematode *Heterodera carotae* is characterized by four phases, commencing with hatching of the cysts in the presence of root exudates given out by the carrot crop. The infesting larvae said to be second stage larvae, "J2", head for and penetrate into the roots and migrate into the central cylinder, form a syncytium and start to develop, passing through the J3 and J4 stages until they reach the adult form. The juvenile of the "J3", third stage, develops inside the cuticle of the J2 stage. Male third stage juveniles appear on the $15^{th}$ day following penetration of the tissues, while the females appear between the eleventh and sixteenth day. Stage 4 juveniles, "J4", exhibit marked sexual dimorphism between the males and females. It should be noted that the development to the adult stage passes through a particular sexual determinism stage, which is epigenetic, 25% of larvae becoming males, 25% becoming females, and the remaining 50% determining their sex as a function of the available food resource conditions, the female sex being preferentially selected if the food conditions are satisfactory. The thread-like males will leave the roots while the females remain attached in the roots, appearing through torn, swollen tissues filled with eggs and being fertilized as soon as they reach maturity. The adult female is considered to appear some 24 days after penetration. The females produce two types of egg, external eggs in which juveniles of the "J1" first stage are formed which mature into "J2" second generation larvae for rapid hatching, infesting the crop afresh, and also internal eggs. When the female dies, its cuticle hardens and turns brown, its body forming a new cyst harbouring the internal eggs. This cyst can remain in the soil for about a decade in the absence of a fresh carrot crop.

The threshold for the appearance of damage in the crop is generally considered to be reached when the presence of one J2 nematode larva is detected per gram of soil.

The carrot is a species with a very wide variability, not only in the cultivated carrot *Daucus carota* subsp. *sativus*, but also in the twelve wild *Daucus carota* sub-species. The wild carrot is a spontaneous plant in many regions of the world (America, Africa, Australia, etc.), but which is principally found throughout Europe and in a large part of Asia.

Cultivated carrots belong to the sub-species *sativus* (*Daucus carota* subsp. *sativus*). Of these, two major types are generally acknowledged, namely oriental carrots known as Asiatic carrots, which are purplish-red, violet (with anthocyanins) or yellowish, and carotene-containing carrots known as Western carrots or European carrots, which are orange, yellow or white in colour. The carrots under current cultivation probably originate from Afghanistan, where they have been known since the $19^{th}$ century. Leading out from this point of origin, they have extended on the one hand to the Near East and China, and on the other hand to the remainder of Western Europe. The carrot was introduced into France from Italy in the fourteenth century. Carrots containing carotene appeared in the seventeenth century in the Netherlands.

Wild carrots can fairly easily be crossed with cultivated carrots and produce fertile hybrids. However, while this variability appears to be available, it is far from being exploited because returning to a cultivated carrot typology, i.e. to a *Daucus carota* subsp. *sativus* plant, is extremely difficult and lengthy.

The inventors have developed an original strategy for disinfecting or disinfestation of soils contaminated by the carrot cyst nematode *Heterodera carotae* which can be used to obtain disinfection levels which are substantially identical to or even superior to those obtained by a chemical disinfection. In this regard, the inventors have developed novel *Daucus carota* plants, which are resistant to the carrot cyst nematode *Heterodera carotae*; they have also demonstrated that by cultivating said plants, it is possible to exploit their resistance in order to disinfect a field contaminated with *Heterodera carotae*; in fact, in an entirely novel manner, the inventors have used resistant plants not with a view to harvesting them, nor of introgressing the trait linked to resistance, but to restrict the multiplication of the carrot cyst nematode *Heterodera carotae*, i.e. they have exploited the nematicidal effect underlying the resistance of these plants, which are not commercial plants, i.e. they are not intended to be harvested for subsequent sale as food, particularly for human consumption. This approach runs counter to the usual methods of breeders, who generally aim to identify, in the wild germplasm, plants which are resistant to a given pest and then to introgress this resistance into the genetic background of commercial plants in order to obtain resistant commercial varieties. In contrast to those methods, the present inventors have not sought to introgress the identified resistance, but to stabilize it and exploit it in order to disinfect soils or cultivation media according to the various uses or methods of the invention. Unexpectedly, the inventors have thus demonstrated that non-commercial resistant plants, i.e. which are not intended to be harvested for subsequent commercialization as a foodstuff, in particular for human consumption, can be considered to be non-chemical phytosanitary products which can be used to disinfect or decontaminate soils infested with the nematode *Heterodera carotae*.

The resistant plants obtained by the inventors in fact appear to cause a blockage of the cycle of the nematode and thus, over time, they reduce infestation of the fields. Without wishing to be bound by any theory, it would appear that the nematicidal *Daucus carota* in accordance with the present invention have a dual action, not only at the syncytium level, by causing a blockage in its development, but also in the males and J2 larvae of *Heterodera carotae*, which appear to be blocked at the roots (necroses).

Since sexual determinism is epigenetic in the carrot cyst nematode *Heterodera carotae*, a blockage of the syncytium will favour the appearance of male nematodes to the detriment of the appearance of female nematodes. The female population will be greatly reduced, and so the possibility of forming new cysts over generations will thus reduce in a similar fashion. In addition and more surprisingly, the inventors have observed that the male and J2 nematodes also appear to be locked in the root. If they cannot leave the root, they cannot fertilize the females and the latter do not produce eggs. The reproductive cycle of the nematode is again interrupted.

Thus, over time, the cysts infesting a plot for cultivation hatch because of the root exudates produced by the resistant plants and release their larvae which are then blocked at their multiplication cycle, and thus cannot produce new cysts. Over a few generations of nematode, for example over one growing season, the level of infestation of the plot reduces to an acceptable level for subsequently receiving a crop of *Daucus carota sativus*.

Definitions

The term "disinfection" or "disinfestation" of a soil or medium in the context of the invention means the reduction in the population of a pest or pathogen, more particularly of a nematode, in particular a carrot cyst nematode, and more specifically *Heterodera carotae* in the soil or medium, or in fact the reduction in its reproduction capacity. The terms "disinfection" and "disinfestation" as regards *Heterodera carotae* are used interchangeably in the present description.

The notions of "resistance" and "susceptibility" are defined in general by the ISF (International Seed Federation).

Thus, the term "resistance" means the capacity of a plant or a variety to restrict the growth and development of a given pathogen or a pest and/or the damage they cause compared with susceptible varieties and under similar environmental and pressure conditions for that pathogen or pest. Resistant plants or varieties may exhibit some disease symptoms or damage under heavy pest or pathogen pressure. Preferably, in the context of the invention, "resistance" means the capacity to restrain the growth and development of a given pathogen or pest.

The term "susceptibility" means the incapacity of a plant or a variety to restrict the growth and development of a given pathogen or pest.

In the context of the invention, the resistance of a plant to the *Heterodera carotae* nematode means the capacity of that plant to restrict the growth and development of said nematode. An example of a plant which is susceptible to that nematode is the carrot variety Nanco sold by Vilmorin.

A plant will be considered to be resistant when it exhibits an absence of multiplication of nematodes and/or a reduction in the multiplication of nematodes, possibly accompanied by the production of males in the vast majority. In the first case, the nematodes are blocked at the level of the initiation of the nourishing syncytium: the larvae do not succeed in "hijacking" the cell metabolism for their profit, and thus cannot complete their cycle. In the second case, certain larvae succeed in initiating then maintaining a nourishing syncytium of poor quality and thus change more into males which demand less energy.

The term "nematicidal/nematicide plant" or nematicidal action or nematicidal capability of a plant principally means the capacity of that plant to reduce the population of a nematode present in a medium, or indeed the capacity to reduce the population corresponding to a stage of development of said nematode, for example the reduction in the number of larvae in the J2 stage, or in fact the reduction in the number of cysts. The nematicidal effect of the present invention is specifically directed towards the carrot cyst nematode *Heterodera carotae*. The nematicidal effect or capability also means the capacity for masculinization of more than 50% of the nematode larvae. A plant with a nematicidal effect is thus a plant which restricts the growth or development of the nematode compared with a *Daucus carota* subsp. *cativus* plant under similar cultivation conditions. It should be noted that the nematicidal effect of the present invention does not derive from the cultivation method per se, but from the capacity of the plant to restrict the multiplication and development of the nematode, in contrast to carrot trap cultivation in which the carrot only acts to attract and channel the nematodes so that they can then be eliminated more easily by pulling up the carrot. The nematicidal effect or capability of the invention is thus obtained by means of a mechanism of resistance of said plants to the carrot cyst nematode *Heterodera carotae*.

The nematicidal effect or capability of a plant against *Heterodera carotae* may, for example, be tested in vitro as described in Example 1B, by inoculating larvae of *Heterodera carotae* directly onto the apex of germinated seeds and counting the number of larvae or the female/male proportion after 15 to 20 days.

Preferably, the nematicidal capability of a plant is demonstrated by planting the seeds into a pot filled with earth with a mean number of 15 larvae per gram of soil; a plant will be considered to be resistant to *Heterodera carotae* or in fact to have a nematicidal action against *Heterodera carotae* if, 90 days after planting, it presents fewer than 10 females, larvae and/or cysts at the roots. The implementation of this test is described in particular detail in Example 2 of the experimental section.

In a population, a population of plants is considered to be generally resistant to *Heterodera carotae* or to have an overall nematicidal capability against *Heterodera carotae* if at least 70% of the plants constituting the population are resistant or have a nematicidal capability as defined above, preferably at least 75%, more preferably at least 80%. A population of plants which is resistant or has a nematicidal capability preferably does not include any multiplicative plants, in particular no plants exhibiting more than 100 larvae in the roots 90 days after planting in a soil comprising an average of 15 larvae or cysts per gram of soil.

The term "sufficiently reducing the level of infestation" of a crop field by the carrot cyst nematode *Heterodera carotae* in order to allow cultivation of carrots means reducing the level of infestation by *Heterodera carotae* below the number of J2 larvae bringing about the appearance of damage to the crop. This threshold is generally one J2 nematode larva per gram of soil, or in fact one nematode cyst per gram of soil.

In a first aspect, the present invention thus concerns the use of a plant from the species *Daucus carota* to treat a soil or a cultivation medium which is infested or susceptible of being infested with nematodes, more specifically carrot cyst nematodes, and more preferably *Heterodera carotae*, with a view to disinfecting it. The plant used in accordance with the invention is a plant with a nematicidal capability or action, in particular against the nematode *Heterodera carotae*. In accordance with a particularly preferred embodiment of the invention, said plant is a *Daucus carota* carrot which does not belong to the sub-species of cultivated carrots *Daucus carota* subsp. *sativus*.

The term "nematicidal plant" as defined above in particular means the capacity to reduce the number of juvenile J2 larvae infesting a medium or the capacity to reduce the number of cysts, or in fact the capacity to bring about masculinization of more than 50% of the larvae of *Heterodera carotae* nematodes infesting a medium. It may also define a combination of these properties, for example the capacity to reduce the number of J2 larvae and the number of cysts, or in fact the capacity to reduce the number of J2 and bring about masculinization; or in fact the combination of these three properties.

Preferably, the masculinization caused by the use in accordance with this aspect of the invention is a masculinization of more than 60%, preferably more than 70%, or even more than 80% of the population of infesting *Heterodera carotae* larvae.

It should be noted that the nematicidal capability or effect is that of the plant or seed and is not the result of the cultivation method; in particular, it does not derive from early pulling of the plants or in fact from cultivation under insufficient irrigation conditions, which are known to cause a reduction in the population of nematodes infesting a soil or in fact a cultivation medium.

This nematicidal capacity is preferably observed during a cultivation period for said carrots of at least 3 months, but preferably of at least 4 months, for example 5 months or in fact 6 months, or even more than 6 months.

As mentioned, in accordance with a particularly preferred embodiment of the invention, the plant used is a *Daucus carota* carrot which does not belong to the sub-species *Daucus carota* subsp. *sativus*; the carrot used for disinfection is thus not a commercial carrot and is not intended to be harvested for marketing as foodstuff, in particular for human consumption, and thus is not intended for consumption. The nematicidal carrot used in the context of the present invention is to be considered to be a disinfecting product or phytosanitary product used to disinfect a soil or cultivation medium infested with *Heterodera carotae* nematodes or susceptible of being infested therewith.

In particular, it may be a plant belonging to the sub-species *Daucus carota dentatus*, or a plant obtained from this sub-species or from another wild sub-species. In particular, it may be a hybrid plant wherein at least one of the two parents is a carrot termed a wild carrot which does not belong to the cultivated sub-species *Daucus carota* subsp. *sativus*; as an example, it may be a nematicidal plant wherein at least one of the two parents is a *Daucus carota dentatus* carrot.

In accordance with a more particularly preferred embodiment, the carrots used in the context of this use are plants obtained from seeds deposited at the NCIMB with accession number NCIMB 42351.

The present inventors have in fact obtained plants with a very high resistance to the carrot cyst nematode *Heterodera carotae*, as illustrated in the experimental section. Said plants have a dual nematicidal action, not only at the level of the development of the syncytium, but also at the level of the males and J2 larvae which appear to be blocked at the level of the roots (necroses). In *Heterodera carotae*, a blockage of the syncytium promotes the appearance of male nematodes to the detriment of the appearance of female nematodes. The female population is drastically reduced; the possibility of forming new cysts over the generations thus reduces in a similar manner. In addition and even more surprisingly, the inventors have established that the male nematodes and J2 larvae also appear to be blocked in the root (necroses). If they cannot leave the root, then they cannot fertilize the females and the latter do not produce eggs. The cycle is yet again interrupted, hence the dual nematicidal action of the plants as described in the experimental section.

Seeds which can be used to obtain *Daucus carota* plants having said nematicidal properties have been deposited by Vilmorin, Route Le Manoir, 49250 La Ménitré, France, in accordance with the requirements of the Treaty of Budapest on the International Recognition of the Deposit of Microorganisms for the Purposes of Patent Protection on 20 Jan. 2015 at the "National Collection of Industrial, Food and Marine Bacteria" (NCIMB), (NCIMB Ltd, Ferguson Building, Craibstone Estate, Bucksburn, Aberdeen AB21 9YA, United Kingdom), with accession number NCIMB 42351, with the reference *Daucus carota* DCHR1.

In accordance with a particularly preferred embodiment, the plants used for the disinfection in accordance with the invention are plants developed from NCIMB 42351 seeds, or in fact plants obtained from or derived from these seeds, after propagation or crossing and selection. The plants used may in particular by *Daucus carota* plants derived from plants originating from seeds deposited under the number NCIMB 42351. The present description provides all of the information necessary to select plants with the nematicidal capability in the context of a selection programme.

The application is also not in any way limited to plants obtained from seeds as they have been deposited. In fact, as described in Example 1 of the application, many wild genotypes are also susceptible of having a resistance to the *Heterodera carotae* nematode, which resistance may be utilized, in accordance with the teaching of the present invention, to disinfect a soil or a cultivation medium.

The plants used in the context of the invention may be a population of nematicidal plants, i.e. at least 70% of the plants of said population have this nematicidal capability, and preferably at least 80% to 90% of the plants, or even more. Thus, it is not excluded for certain plants in the population not to individually have their own nematicidal capability. Preferably, however, the population only comprises a very small percentage, less than 5%, or less than 2% or 1% of plants which are multiplicative for the nematode.

The infested soil or cultivation medium, or soil or cultivation medium which is susceptible of being infested, may be any medium which is suitable for the cultivation of carrots. It may in particular be earth or sand, or a terrain comprising a mixture of earth and sand. A cultivation medium is considered to be infested if it comprises cysts of the *Heterodera carotae* nematode, or if it comprises these nematodes at any other stage of development, for example if it comprises J2 juveniles. A field or a cultivation medium is generally considered to be infested when said field or cultivation medium comprises at least one J2 nematode larva per gram of soil, or in fact one cyst. Beyond this threshold, disinfection is actually considered to be necessary before cultivating commercial carrots intended for food.

However, the use in accordance with the present invention is also applicable to any soil or cultivation medium which is susceptible of being infested. It is, for example, envisageable to operate a disinfection cycle with nematicidal plants in the context of a crop rotation plan. Carrying out such a disinfection systematically before any commercial carrot cultivation or with a view to commercializing the cultivation medium itself may also be envisaged.

With an implementation as described above, then, it is possible to carry out a disinfecting or a disinfestation of a cultivation medium infested by the nematode and thus to reduce the population of nematodes in said cultivation medium by at least 40%, preferably by at least 50%, more preferably by at least 60% and more particularly by at least 75%. It should be noted, however, that the level of reduction of the nematode population carried out by using nematicidal plants in accordance with the present invention is a function of the initial level of infestation of the cultivation medium, of the cultivation period for the nematicidal plants, and also of the density of the nematicidal plants.

Preferably, as detailed above, the nematicidal plants of the invention are cultivated over a cultivation period of at least 3 months, in order to generate the greatest nematicidal capability and preferably at least four months, or even five months or even six months. It is important to note that this cultivation period is distinguished from the cultivation period generally employed in the context of the use of carrot traps. In fact, in such a situation, the cultivated carrot has to be removed from the soil once it has triggered hatching of the cysts present in the cultivation medium but before the formation of new cysts or exodus of many male nematodes from the roots. The use of nematicidal plants as described in the context of the invention is, in contrast, more efficient if the nematicidal carrot remains in the medium for a long time, preferably until the roots are completely mature, over several generations of nematode.

Similarly, the nematicidal plants are planted in a seed density which is comparable to or higher than that used for carrot varieties cultivated for consumption. Particularly appropriate densities in the context of the invention are in the range 0.8 to 4 million seeds per hectare, preferably in the range 0.8 to 2.5 million seeds per hectare. Densities of this type can in fact generate optimized disinfection of the cultivation medium.

In accordance with a preferred embodiment of the invention, the use of nematicidal plants as described means that the number of cysts or in fact of female nematodes in the cultivation medium can be reduced by at least 50%. In fact, the nematicidal plants in accordance with the present invention can also be used to bring about a major masculinization of the larval population without necessarily causing a reduction in their numbers, at least at first. However, the reduction in the number of females to the gain of male larvae then causes a major reduction in the number of cysts in the cultivation medium.

Preferably, the use as described means that the level of infestation of the cultivation medium can be reduced to less than one female J2 *Heterodera carotae* larva per gram of medium or to less than one *Heterodera carotae* cyst per gram of medium. Such a reduction is clearly intended to imply that, before implementing the use in accordance with the invention, a cultivation medium initially comprises more than one female J2 larva or more than one *Heterodera carotae* cyst per gram of medium, for example at least five female J2 larvae and/or *Heterodera carotae* cysts per gram of medium, for example about 10 J2 larvae and/or cysts per gram of medium, or even more than 10 J2 larvae and/or cysts per gram. Infested soils may in fact contain more than 30 or even more than 50 J2 larvae and/or cysts per gram.

Carrots obtained from seeds deposited with number NCIMB 42351 can in particular be used to obtain the preferred implementations described above, and more particularly the reduction in the number of juvenile J2 larvae and/or the reduction in the number of cysts and/or a masculinization of more than 50% of the larvae of the *Heterodera carotae* nematode during a cultivation period of at least 4 months, as well as a reduction in the population of *Heterodera carotae* nematodes in the cultivation medium of at least 60%, more preferably at least 75%, the reduction of at least 50% in the number of cysts or female nematodes in the culture medium as well as the reduction in the level of infestation of the culture medium to less than one female J2 larva of *Heterodera carotae* per gram of medium, as described above. Such plants are, for example, plants obtained by germination of the deposited seeds NCIMB 42351 or in fact by selecting plants with the expected properties from plants obtained from the deposited seeds after one or more crosses.

The use of nematicidal plants as described in the present invention means that disinfection is ensured which is not only suitable from an environmental and ecological viewpoint, but is also reproducible, specific and easy to implementation. It is difficult, for example, to obtain reproducible disinfection with carrot traps. Furthermore, if, under some conditions, the cultivation of commercial carrots can reduce the level of infestation (see Example 9), this reduction is not in any way reproducible (see Example 7, with the same commercial variety).

In accordance with a second aspect, the present invention also concerns a method for disinfecting a soil or cultivation medium, or of reducing the population of nematodes, more particularly carrot cyst nematodes, specifically *Heterodera carotae* in an infested soil or cultivation medium, or which is susceptible of being infested by the carrot cyst nematode *Heterodera carotae*. Said disinfection or disinfestation method is based, in an original manner, on the cultivation of *Daucus carota* plants where said plants have a nematicidal effect on these nematodes.

In accordance with a more particularly preferred embodiment, said disinfection method does not include a step for the application of a chemical product with a nematicidal effect such as 1,3-dichloropropene or its derivatives, in any form thereof. As a consequence, the disinfection is solely the result of the nematicidal action of the cultivated plants.

In accordance with another embodiment, the disinfection or disinfestation method in accordance with the invention may be accompanied by, preceded by, followed by or completed by the application of a nematicidal chemical product. In this case, the principal step of cultivation of nematicidal plants can be used to reduce the dose of nematicidal chemical product which it would have been necessary to use in order to obtain a comparable level of disinfection in the absence of the cultivation of nematicidal plants. In the context of this embodiment, the cultivation of plants in accordance with the invention and the application of the nematicidal chemical product may be concomitant with, successive to or in fact completely or partially overlap; the order of the steps is not a determining factor.

The reduction in the population of *Heterodera carotae* nematodes in a soil or cultivation medium which is infested or susceptible of being infested by the nematode preferably means a reduction in the number of cysts of said nematode in the soil or cultivation medium, or a reduction in J2 juveniles, or a cumulative reduction in both the number of cysts and the number of J2 juveniles in the cultivation medium.

Preferably, the plants cultivated in the context of this disinfection method do not belong to the sub-species of cultivated carrots *Daucus carota* subsp. *sativus*.

Preferred embodiments in the context of the various uses in accordance with the first aspect of the invention are also applicable to the methods in accordance with this second aspect of the invention. In particular, the method is preferably carried out with nematicidal plants of the sub-species *Daucus carota dentatus*, or plants deriving from carrots of the sub-species *Daucus carota dentatus*, for example obtained from an initial cross between a *Daucus carota dentatus* plant and a *Daucus carota sativus* plant.

Regarding the various uses of the invention, the methods are also preferably carried out with carrots which are obtained from or derived from seeds deposited by Vilmorin at the NCIMB on 20 Jan. 2015 with accession number NCIMB 42351. Plants of this type are obtained, for example, by direct germination of said deposited seeds. They may also be plants which are obtained by propagation of carrots deriving from the germination of seeds deposited with the NCIMB or obtained by crossing with other plants, preferably the species *Daucus carota*. Plants of this type are described in the experimental section of the present application. Nematicidal plants for use in the methods of the invention are also plants regenerated, optionally in vitro, from cells from plants obtained by germination of the seeds deposited with number NCIMB 42351.

However, the methods of the invention are not in any way limited to nematicidal plants derived from seeds deposited under the accession number; other *Daucus carota* plants with a nematicidal capability may be used, which are not *Daucus carota sativus*, and which are identifiable in particular by carrying out the tests described in the examples in the experimental section.

As already mentioned, the plants used in the context of the invention may be a population of nematicidal plants.

The soil or cultivation medium which is infested or susceptible of being infested is that described for the uses in accordance with the present invention. It is preferably a field, and may be earth or sand or a mixture of the two, or a sandy terrain.

By carrying out the method in accordance with the invention, then, it is possible to carry out disinfection or disinfestation of a soil or cultivation medium infested by the nematode, and thus to reduce the population of nematodes in said cultivation medium by at least 40%, preferably by at least 50%, more preferably by at least 60% and more particularly by at least 75%. By means of this method, then, it is possible to reduce the level of infestation of the soil or cultivation medium to less than one female J2 larva and/or cyst of *Heterodera carotae* per gram of medium, i.e. below the threshold corresponding to a medium which is said to be "infested". The method is preferably carried out on a cultivation medium comprising more than one J2 larva and/or cyst per gram of medium, preferably at least 5 J2 larvae and/or cysts per gram of medium, or approximately 10 or more than 10.12 larvae and/or cysts per gram of medium, or even 20, 25, 50 or more.

In accordance with a preferred embodiment of the invention, the method can be used to reduce the number of cysts or in fact of female nematodes in the cultivation medium by at least 50%. The reduction in the number of females may be due to an overall reduction in the number of nematodes, or due to a reduced proportion of females with respect to the males. In fact, the nematicidal plants in accordance with the present invention may bring about a major masculinization of the population of larvae without necessarily bringing about an immediate reduction in their numbers, at least initially. However, the reduction in the number of females to the gain of the number of male larvae then brings about a drastic reduction in the number of cysts in the soil or cultivation medium.

The method in accordance with the invention comprises cultivation of nematicidal plants for at least 3 months and preferably for a period of at least 4 months, preferably at least 5 months, more preferably at least 6 months. As disclosed with regard to the uses in accordance with the invention, this cultivation period is very different from the cultivation periods applicable in the context of carrot trap cultivation, where maintaining the carrot traps beyond 3 months results in a multiplication of the number of infesting cysts or larvae instead of reducing them. The method in accordance with the invention is, in contrast, much easier to implement in that the nematicidal carrots can be removed at any time, preferably after 4 months, without any prejudicial effect on the level of infestation. In fact, irrespective of the time at which they are pulled up, preferably, however, after 3 months, a reduction in the level of infestation of the cultivation medium will always be obtained. The optimized nematicidal effect is obtained when approximately one cultivation period corresponding to a complete cycle of cultivation for a commercial variety of carrot *D. carotae* has been carried out, i.e. approximately 6 months. However, a good nematicidal effect is already observed after 3 months of cultivation, preferably after 4 months. The optimal pulling time, taking into account on the one hand the absence of commercial production during the cultivation period for the nematicidal carrots, and on the other hand the optimized nematicidal effect, appears to be between 4 and 6 months. Clearly, this optimized period has to be determined by also taking into account the probability of infestation of the cultivation medium and its level of infestation.

In accordance with the present method, the nematicidal plants are planted in a seed density which is comparable to or higher than that used for carrots termed commercial carrots, cultivated for consumption. Particularly appropriate densities in the context of the invention, when they are sown in the fields, are in particular those in the range 0.8 to 4 million seeds per hectare, and preferably in the range 0.8 to 2.5 million seeds per hectare. Densities of this type can in fact be used to generate an optimized disinfection of the cultivation medium. Other densities may be envisaged, however, in particular when small quantities of cultivation medium are used, or in fact when the level of infestation is particularly high, or indeed particularly low. The density may also be adapted as a function of the composition of the cultivation medium.

When carrying out the invention, cultivation of the nematicidal carrots may be initiated at any opportune moment, depending on the crops preceding and following cultivation of the nematicidal carrots. In accordance with preferred embodiments, said cultivation is, for example, initiated in autumn or in winter, in order to provide the best nematicidal yield and/or the least impact on reliability. Depending on the climate or other constraints, for example economic constraints, the cultivation may, however, be initiated at other times if this turns out to be appropriate, necessary or desirable. The cultivation is preferably initiated by planting the seeds, although they may also be pricked out.

The method in accordance with the present invention may be used to obtain a reduction in the nematode population, in particular that of females, of *Heterodera carotae* in an infested cultivation medium essentially by means of the nematicidal properties of the cultivated plants. As detailed above, this characteristic of the method is in particular distinguished from the cultivation of carrot traps, where the reduction in the population of nematodes is linked to the cultivation method and more particularly to the time of pulling, but not to the cultivated plants.

Certain measures may, however, be taken in the context of the invention in order to amplify the reduction in the nematode population; in particular, certain cultivation conditions or in fact certain fertilizers etc., may be applied in order to amplify the nematicidal effect brought about by the nematicidal plants in accordance with the invention. In particular, the plants may optionally be cultivated under insufficient hygrometric conditions, because a certain dryness of the cultivation medium is known to contribute to reducing the population of *Heterodera carotae* nematodes.

Alternatively, the method may be carried out under hygrometric conditions which are satisfactory for the cultivation of commercial carrots.

Carrots obtained from seeds deposited with the number NCIMB 42351 can in particular be used to obtain the preferred embodiments described above for the various methods in accordance with the invention, in particular plants obtained by germination of the deposited seeds.

In accordance with a further aspect, the present invention also concerns a population of *Daucus carota* plants or a population of *Daucus carota* carrot seeds deriving from or obtained from seeds deposited under the accession number NCIMB 42351, where said population or said carrots has/have a nematicidal effect on the nematodes, in particular carrot cyst nematodes, and specifically *Heterodera carotae*. The nematicidal effect is as described in the present application. Plants from deposited seeds are in particular plants obtained by germination of said seeds. "Plants or seeds deriving from or obtained from deposited seeds" also encompasses plants or seeds obtained by crossing or propagating plants obtained by germination of deposited plants, as well as all plants derived from plants obtained by germination of deposited seeds, with the condition, however, that they have a nematicidal capability and in particular the nematicidal capability as described for the plants corresponding to the deposited seeds and illustrated in the experimental section of the application.

The present invention also concerns fragments of these plants, germs, reproductive material and cells of these plants, which can be regenerated to obtain resistant plants or nematicides in accordance with the invention.

Preferred embodiments of the invention have already been described in the context of the above aspects of the invention; they are all applicable to this aspect of the invention. In particular, the nematicidal effect of the plants in accordance with this invention is preferably a reduction in the number of J2 juveniles and/or a reduction in the number of cysts and/or a masculinization of more than 50% of the larvae of the nematode *Heterodera carotae*, preferably over a cultivation period for said carrots of at least 3 months.

Said population comprises at least 70% of plants which individually have a nematicidal capability as described, or 70% of seeds giving rise to such plants. Preferably, the proportion is more than 70%, for example at least 80%, or even at least 90% or more.

Preferably, however, the population has only a very small percentage of less than 5% or less than 2% or 1% of multiplicative plants for the nematode, or seeds giving rise to such plants.

As detailed above, the present invention is illustrated by the *Daucus carota* plants identified by the inventors and having a resistance to the nematode, in particular to the carrot cyst nematode *Heterodera carotae*; however, the invention is not limited to the genotype identified by the inventors. In fact, other plants which also have a nematicidal capability may readily be identified by the person skilled in the art. To this end, a suitable test for determining the nematicidal capability of a plant or of a population or of selecting plants with such a capability is as follows:

planting the seeds to be tested into a pot filled with earth infested with about 10 to 15 *Heterodera carotae* larvae per gram of soil;
cultivating for 70 to 90 days under normal cultivation conditions;
70 to 90 days after planting, pulling up the plants and counting the number of J2 females in the roots.

A plant with a nematicidal capability in accordance with the invention is preferably a plant with 0 to 10 females in the roots at the end of this test. In contrast, a plant with more than 100 females in the roots will be considered to be a multiplicative plant.

Using this protocol, it is easy to identify nematicidal plants or to select nematicidal plants, in particular in a selection programme.

The present invention also pertains to a phytosanitary product for disinfecting or disinfestation of a soil or a cultivation medium, said product comprising nematicidal or resistant plants as described in the context of the invention. All of the characteristics described above may be applied to this aspect of the invention.

In particular, a phytosanitary product as mentioned may comprise a population of *D. carota* plants or seeds, and preferably which is not from the sub-species *Daucus carota* subsp. *sativus*, at least 70% of them having a nematicidal effect or capability.

Particularly advantageously, the phytosanitary product does not include multiplicative plants as described above.

Thus, the present invention is characterized, inter alia, by the fact that non-commercial *D. carota* plants are cultivated or used, i.e. they are not intended to be harvested for food, in particular for human consumption, and the resistance of these plants to *Heterodera carotae* is exploited in order to obtain a nematicidal effect and to allow disinfection of a field infested with that nematode.

KEY TO FIGURES

FIG. 1: The graph illustrates, for various hybrid combinations obtained from genotypes identified in Example 1, as well as for the susceptible variety Nanco, the distribution of the number of *Heterodera carotae* females per plant, the mean number of females per plant and the percentage of plants with less than 10 *Heterodera carotae* females.

Figure 2:
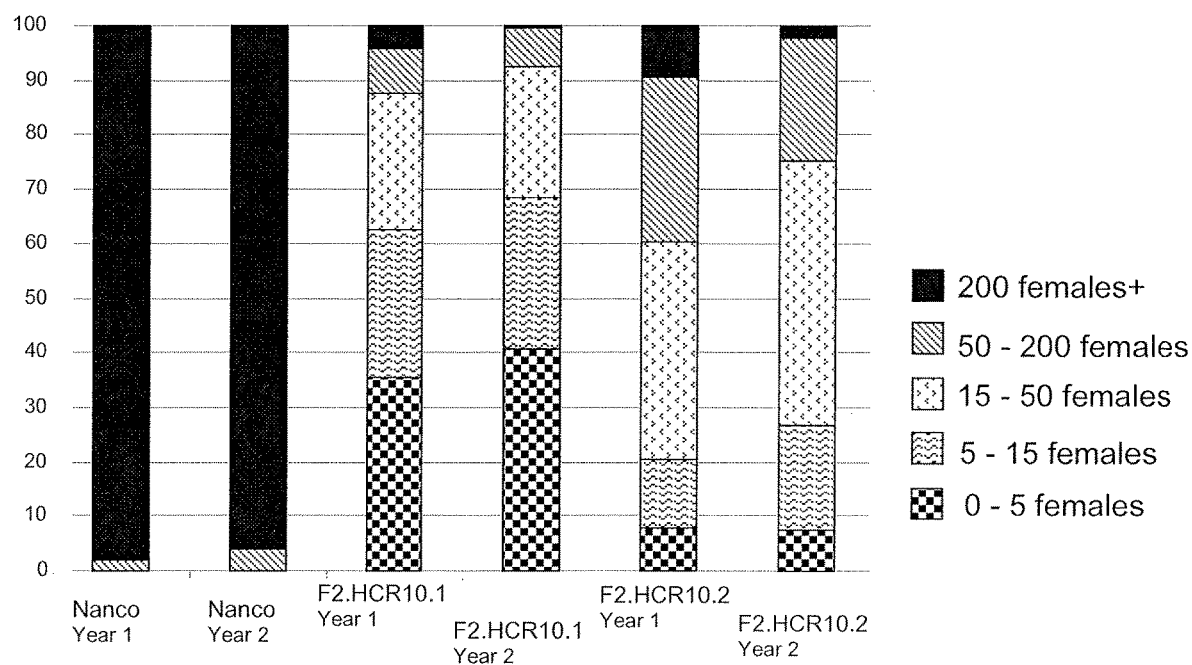

FIG. 2: The table indicates, for the two F2 lines obtained from the HCR10 genotype, the distribution of the number of females as an average per plant over two years of cultivation.

Figure 3:
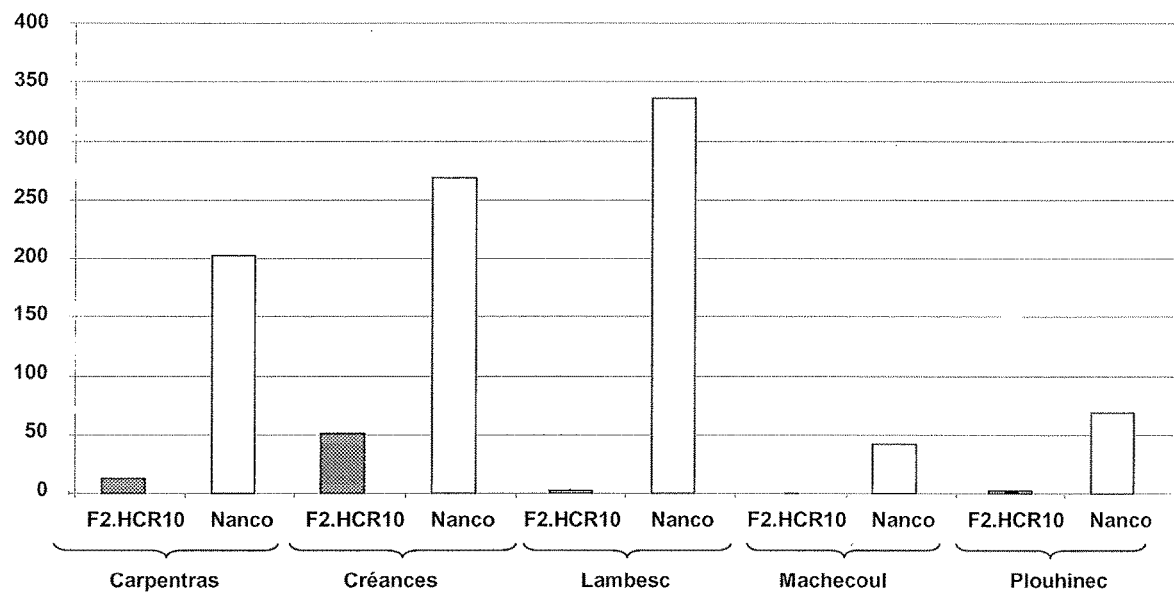
Figure 4:
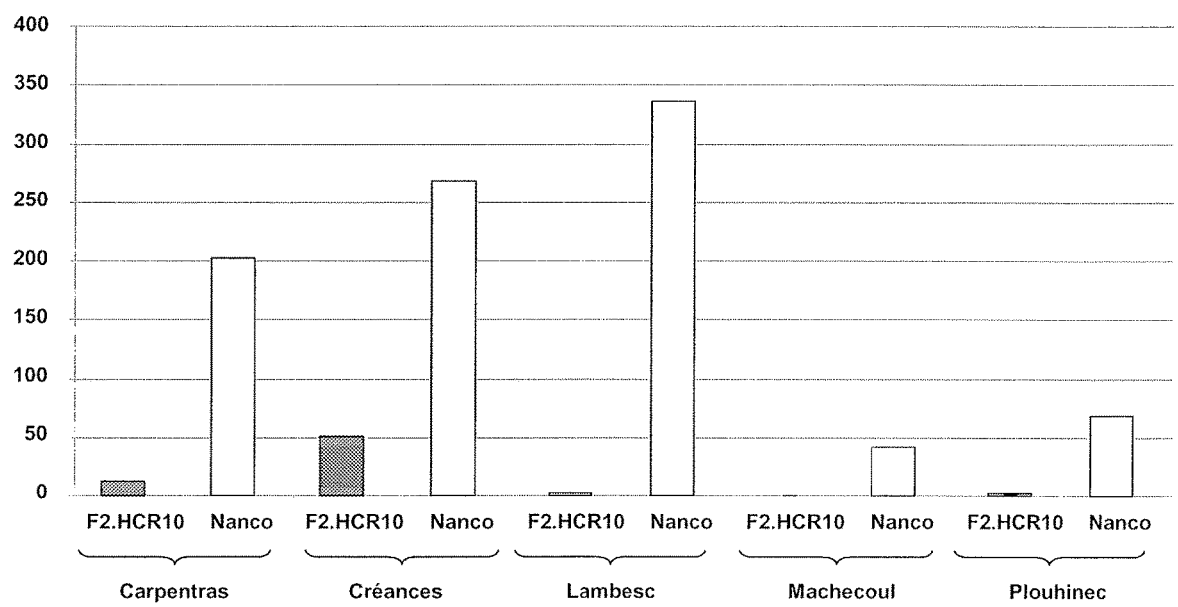

FIGS. 3 and 4: These figures describe the mean number of females present in the roots, approximately 80 to 90 days after planting in infested cultivation media taken from 5 distinct geographic zones in crop fields infested with *Heterodera carotae* in Créance in the Manche department, Plouhinec in the Morbihan department, Machecoul in the Vendée department, Carpentras in the Vaucluse department and Lambesc in the Bouches-du-Rhone department. Their level of contamination varied from 4.46 to 13.86 J2 larvae per gram of soil. FIG. 3 concerns plantings on $3^{rd}$ May with readings on $19^{th}$ July, while FIG. 4 concerns plantings on $28^{th}$ May with readings on $24^{th}$ August.

Figure 5:
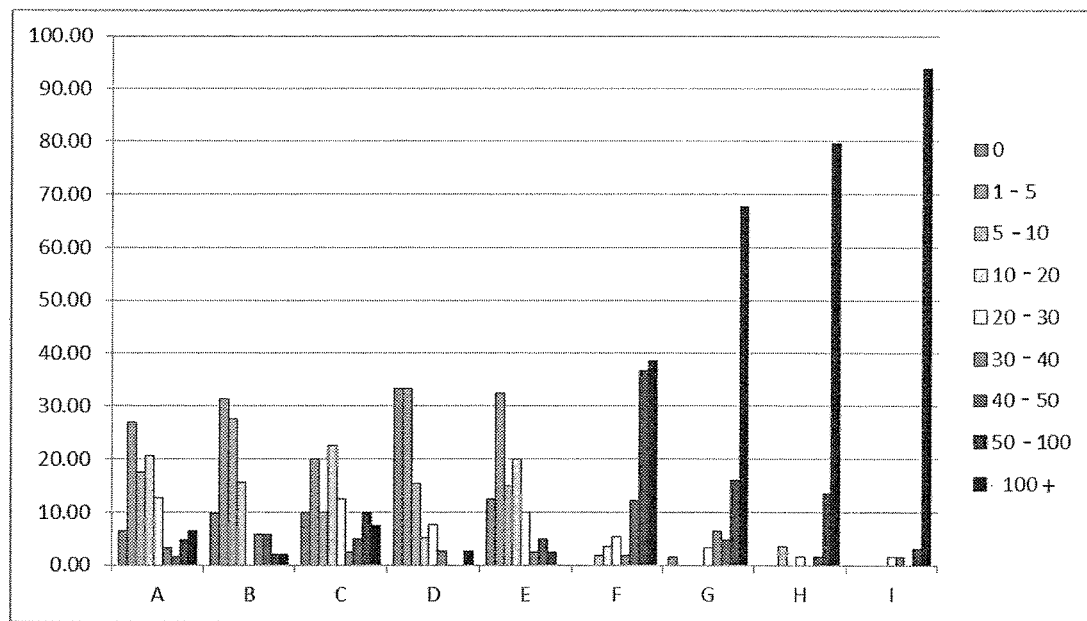

FIG. 5: FIG. 5 illustrates the results shown in Table 2. Along the abscissa are the various genotypes A to I which were tested. Up the ordinate is the percentage of plants in a genotype belonging to each of the following 9 classes: 0; 1 to 5 females; 5 to 10 females; 10 to 20 females; 20 to 30 females; 30 to 40 females; 40 to 50 females; 50 to 100 females and 100 to 1000 females.

Figure 6:
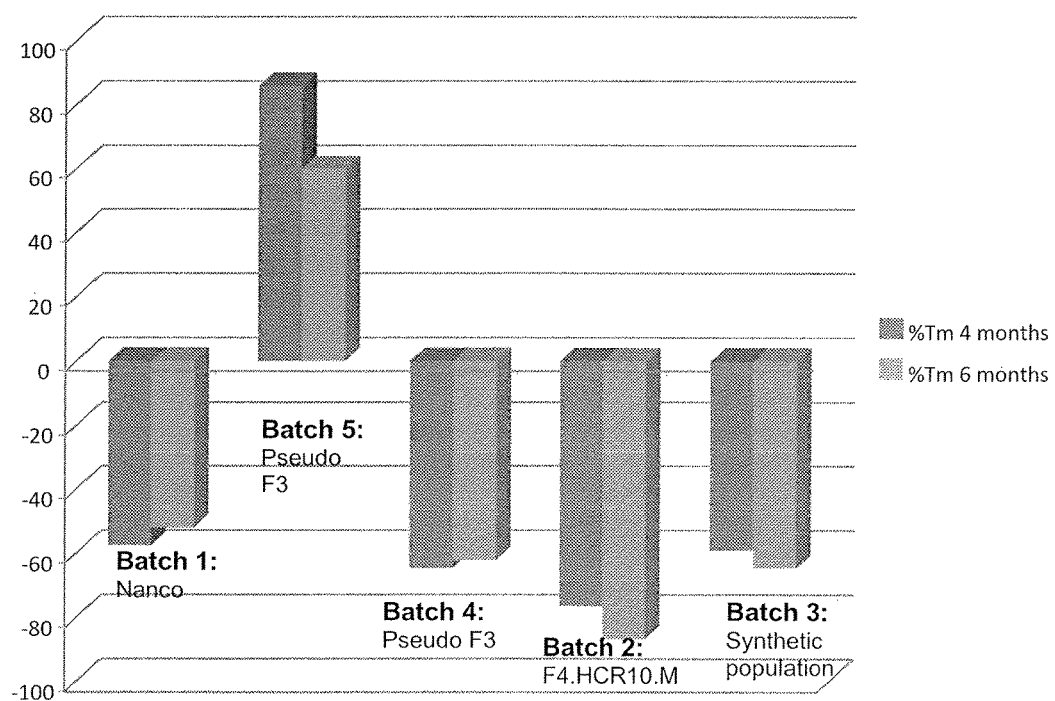

FIG. 6: FIG. 6 illustrates the degree of multiplication of cysts in the soil of planters in which various batches of seeds, susceptible and resistant, were cultivated, after 4 months and 6 months of cultivation. The level of infestation at the time of planting is identical in each planter. "% Tm" indicates the level of multiplication of the cysts in the soil.

EXPERIMENTAL SECTION

Example 1: Identification of Plants Resistant to *Heterodera carotae*

The inventors proceeded in three successive steps.

Firstly, they tested more than 3700 different plants of various genetic and geographical origins using a root inoculation test. Only plants presenting no female *Heterodera carotae* nematode, particular no cysts, were retained for the second analysis (test for confirmation of resistance in vivo).

A. Obtaining *Heterodera carotae* Juveniles (J2)

The cysts were harvested in infected plots in lower Normandy and multiplied in greenhouses before being stored at 4° C. prior to use. The cysts were then moistened in water over 24 h before being transferred into carrot root exudate and deposited in an air-conditioned chamber at 20° C. The larvae, a maximum of one week old, were recovered and stored at 4° C. in water.

B. Decontamination of Carrot Seeds and Inoculation of *Heterodera carotae* Larvae (Step 1)

The carrot seed decontamination was carried out at 52° C. in a water bath for 18 minutes in sterile water supplemented with 10% SDS. The seeds were then rinsed in sterile water and deposited onto 1.5% gelose medium.

Germinated seeds were transferred individually into a Petri dish on gelose medium supplemented with microelements, MS medium (Murashige T and Skoog F (1962)). The J2 stage juvenile *Heterodera carotae* were inoculated onto the plantlets which had a root length of 1 to 2 cm.

Seven J2 were deposited on the apex of the root using a fine brush. The dishes were left in the laboratory for 48 h before being deposited in an air-conditioned chamber at 20° C. for an irradiation period of 16 h.

60 seeds were germinated for each genotype (plant) tested. The number of plants actually evaluated (inoculated) for their resistance then depended on the degree of germination obtained in the Petri dishes.

A commercial hybrid *Daucus carota sativus* susceptible to the carrot cyst nematode was used as the susceptible control. The Nanco variety was selected as the susceptible control for this purpose.

The dishes were observed between 15 and 20 days after inoculation with the second stage (J2) juveniles. All of the plants which had not allowed the development of nematodes or which had only allowed the development of males were retained. Plants with females were eliminated.

C. Resistance Confirmation Tests (Steps 2 and 3)

Step 2:

The plants retained at the end of the in vitro test were re-potted into an earth-sand mixture before being tested a second time in vivo in a natural soil contaminated with *Heterodera carotae* cysts.

The device was constituted by a PVC tube 20 cm long and 4.5 cm in diameter containing a sandy soil (70% sand and 30% earth). The assembly was placed on a bed of Fontainebleau sand, kept moist to keep the humidity constant. The plants were pricked out in contact with a pack of 10 cysts of *Heterodera carotae* obtained from the same population as during the in vitro test. The pack could advantageously be replaced by adding larvae in solution directly to the base of each plant. The test was carried out in a greenhouse under controlled temperature conditions of 20° C.±5° C. and with an irradiation period of 16 hours.

Two months after planting, the plants were checked one by one for their resistance to *Heterodera carotae* by observing the roots, which meant that the presence or absence of females could be detected, particularly the presence or absence of cysts. The plants with developed females, particularly cysts, were automatically eliminated because they were susceptible; the others were retained as they were potentially resistant.

Of 3720 different plants which were tested, only 32 were retained as this step.

Step 3:

Thirdly, the 32 retained plants were initially multiplied in vitro using somatic embrogenesis protocols which are well known to the person skilled in the art; see, for example, Steward, F. C. et al (1958), then four clones of each genotype were re-potted into an earth-sand mixture containing cysts of *Heterodera carotae* in accordance with the test of step 2.

Only the genotypes which did not present a female *Heterodera carotae* nematode, in particular no cyst, on none of the 4 cloned plants was retained: 11 genotypes were finally retained at the end of these three successive steps. They are presented in Table 1 below.

TABLE 1

Tested genotypes with a resistance to *Heterodera carotae* (HCR = *Heterodera carotae* Resistance)

| Number of genotype | Sub-species |
| --- | --- |
| HCR1 | *Daucus carota gummifer* |
| HCR2 | *Daucus carota carota* |
| HCR3 | *Daucus carota carota* |
| HCR4 | *Daucus carota carota* |
| HCR5 | *Daucus carota gummifer* |
| HCR6 | *Daucus carota carota* |
| HCR7 | *Daucus carota gummifer* |
| HCR8 | *Daucus carota commutatus* |
| HCR9 | *Daucus carota commutatus* |
| HCR10 | *Daucus carota dentatus* |
| HCR11 | *Daucus carota gummifer* |

The inventors retained and multiplied these 11 genotypes in vitro.

Example 2: Validation and Identification of Resistance to *Heterodera carotae*

The 11 plants retained in the preceding step were crossed with plants of the cultivated carrot *Daucus carota sativus* susceptible to *Heterodera carotae* in order to study the heritability of the resistance.

The first generation hybrid plants obtained from crossing resistant genotypes with susceptible *Daucus carota sativus* plants were sown into pots in earth removed from fields naturally infested with *Heterodera carotae*. The mean level of *Heterodera carotae* infestation for this earth was 16 larvae per gram of soil. Before planting, the seeds were decontaminated in water at 51° C. for 12 minutes. The pots were placed in a greenhouse, at a temperature of 20° C. 100 seeds per hybrid combination that was produced were employed.

The plants were analysed 70 to 90 days after planting; the root system of each plant was carefully washed then followed with a jet of water applied to the roots in order to detach the adult and stage J4 females.

It was observed that 70% of the hybrid plants with the HCR10 genotype as a parent plant had fewer than 10 females in the roots. The results are shown in FIG. 1 for a few combinations of hybrids as well as for Nanco, the susceptible variety selected as the control: the table shows, for each hybrid combination, the distribution of the number of *Heterodera carotae* females per plant, the mean number of *Heterodera carotae* females per plant and the percentage of plants with fewer than 10 *Heterodera carotae* females.

Only plants with a reduced number of 0 to 5 female *Heterodera carotae* larvae were retained and self-pollinated to produce second generation plants.

The second generation was tested under identical conditions to those of the tests for the first generation, sown into pots, into earth removed from fields naturally infested with *Heterodera carotae*. The mean level of *Heterodera carotae* infestation of this earth was 55 larvae per gram of soil. The control Nanco behaved as expected, with more than 97% of the tested control plants having more than 200 *Heterodera carotae* females. The analysis of second generation plants obtained from the HCR10 genotype showed high levels of resistance, more than 80% of the plants having fewer than 100 *Heterodera carotae* females. The analysis was repeated over two years, the results being substantially identical and being presented in FIG. 2. This figure illustrates the distribution of the number of females over two years for two F2 lines obtained from the HCR10 genotype.

Again, only the plants with a reduced number of larvae but this time 0 to 10 *Heterodera carotae* females were retained and self-pollinated to produce third generation plants.

Similarly, the third generation plants were sown into pots in earth removed from fields naturally infested with *Heterodera carotae*. Only plants with a reduced number of 0 to 10 females per plant of female *Heterodera carotae* larvae were retained.

During the tests and generations, the inventors identified the HCR10 genotype as being a potential source of resistance to *Heterodera carotae*. The multiplication of nematodes was very restricted in this genotype: not only are larvae blocked in the J2 stage, but also they are highly masculinized, thereby demonstrating a nematicidal action for said plants. The third generation plants with the HCR10 genotype were again phenotypically very close to the wild type; they had white roots which were very slightly tuberized with waxy and glossy foliage and a spreading growth habit.

Example 3: Stability of Resistance Compared with Various *Heterodera carotae* Populations The second generation plants obtained from the HCR10 genotype (F2.HCR10) were used for this analysis: they were sown into pots into earth removed from naturally infested fields but of multiple geographical origins representing various French cultivation zones where *Heterodera carotae* is present. The susceptible variety Nanco was used as the susceptible control.

The 5 populations of *Heterodera carotae* were taken from crop fields infested with *Heterodera carotae* from Créance in the Manche department, Plouhinec in the Morbihan department, Machecoul in the Vendée department, Carpentras in the Vaucluse department and Lambesc in the Bouches-du-Rhône department. Their level of contamination varied from 4.46 to 13.86 larvae J2 per gram of soil.

FIGS. 3 and 4 describe the mean number of females present in the roots. The plants were analysed approximately 80 to 90 days after planting. The plants were carefully pulled up then the root system of each plant was carefully washed. Finally, the cysts were counted using a binocular magnifying glass.

This experiment shows that the second generation plants obtained from the HCR10 genotype had a resistance against the various populations of *Heterodera carotae* which were tested.

Example 4: Identification of Resistance Mechanism

Clones of resistant plants were pricked out into a soil contaminated with *Heterodera carotae* cysts. The clones of a susceptible control served to monitor the dynamics of penetration of the nematode by means of an inspection, under a microscope, of the roots at different times after the start of the experiment. The inventors observed that the larvae were blocked at the J2 stage and also that they were strongly masculinized.

Example 5: Greenhouse Tests and Validation

The aim of this experiment was to test the level of resistance of various plants:

second (F2.HCR10), third (F3.HCR10) and fourth (F4.HCR10) generation plants described or obtained as described in Examples 1 to 3 (genotypes A, B and E, respectively), third generation plants obtained from brother-sister crosses obtained by crossing a second generation plant with the HCR10 genotype, selected for its high level of resistance, with another second generation plant with the HCR10 genotype selected for its high level of resistance (genotypes C and D, corresponding to AxA), hybrid plants obtained by crossing a second generation plant with the HCR10 genotype selected for its high level of resistance with fertile male lines of the carrot *Daucus carota sativus* susceptible to the nematode *Heterodera carotae* (genotypes F, G and H);

genotype I, corresponding to the susceptible control Nanco.

The plants were sown in three distinct series (with the exception of genotypes D and E which were sown in two series of the 3) in an amount of approximately 20 plants per series for each genotype, into plastic (8*8*8) pots containing about 380 g of soil which had previously been homogenized in a cement mixer. The soil was naturally infested and came from Créance, in the Manche department. The mean measurement of the level of infestation was J2 larvae per gram of soil. Watering was carried out pot by pot, from above.

The test was inspected between 70 and 90 days after planting using a rapid reading method: counting all of the females (including cysts) for plants with fewer than 100 females. Counting was stopped above this value of 100 females and the value "more than 100" attributed to those plants.

Plants obtaining a score of fewer than 5 females were retained and pricked out into a mixture of earth and sand free from contamination.

The series were sown at specific times between September and November.

The results are shown in Table 2 which, for each series, summarizes the plants as a function of their level of infestation ("classes" of plants with 0 females, 1 to 5 females, 5 to 10 females, etc.). Thus, for genotype A, 4 plants out of 63 tested plants did not present any females, 17 plants had 1 to 5 females, etc.

The genotype A corresponded to the resistant genotype (resistant second generation plant obtained from HCR10 genotype), while the genotype I corresponded to the susceptible control. For the three series, the level of control was sufficiently high for the test to be considered to be discriminating.

The mean M represents the total number of cysts counted for each plant of each series, divided by the number of plants analysed per genotype.

The mean distribution between the various classes is illustrated in FIG. 5 for each of the tested genotypes.

TABLE 2

Number of cysts per plant for various genotypes.

| Class | Genotypes | | | | | | | | |
|---|---|---|---|---|---|---|---|---|---|
| | A | B | C | D | E | F | G | H | I |
| 0 | 4 | 5 | 4 | 13 | 5 | 0 | 1 | 0 | 0 |
| 1 to 5 | 17 | 16 | 8 | 13 | 13 | 0 | 0 | 0 | 0 |
| 5 to 10 | 11 | 14 | 4 | 6 | 6 | 1 | 0 | 2 | 0 |
| 10 to 20 | 13 | 8 | 9 | 2 | 8 | 2 | 0 | 0 | 0 |
| 20 to 30 | 8 | 0 | 5 | 3 | 4 | 3 | 2 | 1 | 1 |
| 30 to 40 | 2 | 3 | 1 | 1 | 1 | 1 | 4 | 0 | 1 |
| 40 to 50 | 1 | 3 | 2 | 0 | 2 | 7 | 3 | 1 | 0 |
| 50 to 100 | 3 | 1 | 4 | 0 | 1 | 21 | 10 | 8 | 2 |
| 100 to 1000 | 4 | 1 | 3 | 1 | 0 | 22 | 42 | 47 | 61 |
| S | 63 | 51 | 40 | 39 | 40 | 57 | 62 | 59 | 65 |
| M | 21.397 | 13.3529 | 28.275 | 12.538 | 12.075 | 85.421 | 86.371 | 92.4375 | 323.615 |

The results were as follows, for each genotype tested:

A: (F2.HCR10) resistant control genotype. The results were in agreement with those obtained in the preceding tests, with a high level of resistance (general mean over the 3 series of 21.4) and the presence of a small percentage of multiplicative plants (about 10%) at the tail of the distribution.

B: (F3.HCR10, F3 derived by self-fertilization of the F2.HCR10 population) genotype of interest for the 3 series with approximately 50% of plants having fewer than 10 females. However, the presence of a small percentage of multiplicative precursors (approximately 10%) at the tail of the distribution should be noted.

E: (F4.HCR10, F4 derived by self-fertilization of the F3.HCR10 population) highly resistant genotype (general mean over the two series of 12.5). Note the total absence of multiplicative plants at the tail of the distribution.

From one generation to another (F2, F3 then F4), an increase in resistance and a reduction in the number of multiplicative plants was observed.

C: Atypical profile with a practically equivalent percentage of plants in all classes. This type of profile tends to indicate an oligogenic character for the resistance.

D: Highly resistant genotype (general mean over two series of 12.5). note the almost complete absence of multiplicative plants at the tail of the distribution.

F, G and H: Identical profile to that of susceptible control I.

These three genotypes (F, G, H) were obtained from a cross with a commercial elite line susceptible to *Heterodera carotae*; the results show that the resistance is recessive. In consequence, the self-crossing of individuals obtained from the HCR10 genotype meant that individuals could be obtained which were homozygous for the resistance characteristic in the case of a monogenic resistance. Since the resistance is more likely to be oligogenic, though, the inventors carried out crosses in order to stabilize a resistant descendancy.

Example 6: Container Tests

The aim of this experiment was to test the nematicidal capability of third generation plants with the HCR10 genotype.

F3 plants were planted in 5 lines of planting in containers (32*28*20 cm) comprising 18 cm of naturally infested soil (and originating from Créance). The infestation was measured at the start and at the end of the experiment after pulling, for each container. The experiment was carried out twice.

| | Rep 1 | Rep 1 | Rep 2 | Rep 2 |
|---|---|---|---|---|
| Genotype | Genotype I susceptible | Genotype B | Genotype I susceptible | Genotype B |
| Pop initial (J2/g) | 10.92 | 18.80 | 10.6 | 22.07 |
| Pop final (J2/g) 3 February | 14.46 | 9.86 | — | — |
| Pop final (J2/g) 28 March | | | 27.51 | 9.33 |
| Tm (Pf/Pi) | 1.32 | 0.52 | 2.59 | 0.42 |
| % | +32.5 | −47.53 | +159 | −56 |

Susceptible genotype I (Nanco): in agreement with expectations, an increase in the soil population of *Heterodera carotae* was observed after pulling up the carrots. This increase was even higher when the cultivation period was longer (+32% and +159%), which corresponded to producing an additional generation in the case of the second harvesting date. Genotype B: In both cases, the level of the population reduced by approximately 50%. The reduction was all the more marked with a longer period. The results could have been even better if the genotype used had been more genetically homogeneous: the test of Example 5 shows that approximately 10% of the plants were multiplicative for this genotype. However, these results are extremely encouraging and are on the level of those obtained in the case of a successful trap cultivation carried out with a conventional variety. With a conventional variety however, destroying the crop too late causes the opposite effect to that desired, i.e. maintains or increases the population, as confirmed with the susceptible genotype I.

With other genotypes (in particular the genotypes E or D, free from multiplicative plants), values close to those obtained in the case of chemical disinfection (80-90%) should be able to be obtained in this test.

Example 7: Validation of Nematicidal Capability

An artificial greenhouse test was carried out in order to measure the level of the nematicidal capability of a carrot crop resistant to *Heterodera carotae* identified in the preceding examples.

Protocol:

This test was carried out in planters containing naturally contaminated soil from the Créance region (Normandy). The criterion measured was the level of infestation of the soil (number of cysts) at planting then at various dates after planting, which meant that a level of multiplication of the *Heterodera carotae* nematode could be measured during cultivation. The method used was of the complete block randomization type with 2 repeats per genotype.

Plant Material Tested:

Susceptible control: Nanco

Resistant Plants:

2 different batches of F3.HCR10 (genotype B in Example 5): F3.HCR10a and F3.HCR10b;

2 different batches of plants obtained from F3.HCR10 by multiplication: F3.HCR10.Ma and F3.HCR10.Mb Results:

The inventors observed very poor germination when this test was being carried out: 33-34% for Nanco and 0 to 14% for the 4 resistant F3 lines, including 0% for the F3.HCR10b line. This poor level of germination observed for all of the test plants was probably linked to the poor conditions during germination.

The inventors observed that with Nanco, the susceptible control, the increase in the nematode population was 430% after 6 months of cultivation, despite the poor germination conditions. For the lines F3.HCR10a and F3.HCR10.Ma, a reduction in the level of infestation of the soil by approximately 20% (F3.HCR10.Ma) to approximately 40% (F3.HCR10a) was observed after 6 months of cultivation despite the poor germination conditions.

Conclusion:

The nematicidal capability is confirmed by this test.

However, given the very poor germination during this test, it was not possible to draw any accurate conclusions regarding the level of the nematicidal capability of this *Heterodera carotae*-resistant material.

Example 8: Creation of Batches of Seeds with the Most Resistant Genotypes

Multiplication of the best F3s which were identified was carried out in large cages and in a plastic tunnel (fertilization carried out randomly by insects), with a view to depositing seeds, in order to obtain:

a synthetic population created by intercrossing the most resistant F3 plants;

a population F4.HCR10.M, corresponding to a multiplication of the F4.HCR10 line described in Example 5 for which the nematicidal capability had been ascertained.

The seeds deposited on 20 Jan. 2015 at the NCIMB, with accession number NCIMB 42351 and reference *Daucus carota* DCHR1, corresponded to a multiplication of the F4.HCR10.M population, baptised F4.HCR10.MM.

Example 9: New Validation of Nematicidal Capability in Planters

This test was carried out in order to test the nematicidal effect of a carrot population on *Heterodera carotae*. It was carried out in planters, each genotype being tested in a planter over two rows. In order to guarantee the robustness of the test, it was carried out twice.

The nematicidal effect was monitored by counting the number of cysts in the earth infected by means of sampling before planting, half way through the test 4 months after planting, and at the end of the test 6 months after planting, which meant that the degree of multiplication of the nematode *Heterodera carotae* during cultivation could be measured.

Inoculum:

Natural inoculum: earth from a field infested with *Heterodera carotae* nematodes. This inoculum was homogenized well in a cement mixer.

Preparation of Planters:

29 litre apertured planters, H: 20 cm, L: 98 cm, W: 25 cm (1 planter per genotype and per repeat) were filled with strictly the same quantity of earth.

Plant Material Tested:

Batch 1. Nanco: susceptible control

Batch 2. Resistant F4 line (F4.HCR10.M, see Example 8)

Batch 3. A synthetic population as described in Example 8

Batch 4. Pseudo resistant F3 line

Batch 5. Pseudo resistant F3 line

Planting: the seeds were planted leaving a 5 cm space between the seeds and the edge in order to avoid a border effect. Planting was carried out in two parallel 70 cm rows with 60 seeds per row distributed homogeneously over the entire length.

Samples: during the test, 3 samples with 3 specimens in each planter were taken. Specimen number 1 corresponded to sampling before planting, No. 2 corresponded to sampling 4 months after planting and No. 3 corresponded to sampling 6 months after planting.

Results:

The inventors observed good germination for all of the batches tested except for batch 4 (25%), but very poor development of the plants for the susceptible control Nanco (very significant growth retardation). Because of the lateness of the growth of the susceptible control, the results for multiplication of nematodes do not agree with the results obtained in preceding years in this type of test. In fact, the retarded growth results in the introduction of a bias into the results: while in all of the preceding tests a multiplication of the nematode in the soil was observed (from 159% to 430% for the susceptible controls), here a reduction of 52% in the nematodes was observed. The poor development of the roots probably had an impact on the cycle of the nematode.

3 of the genotypes tested had a reduction in the level of infestation in the soil of 62% to 87% after 6 months of cultivation;

for one of the genotypes (batch 5, pseudo resistant F3), there was an increase in the nematode population of 60% after 6 months of cultivation, which was unexpected.

The results are illustrated in FIG. 6. The tables below record the analysis of the variance and the results of a Newman-Keuls test with a 5% threshold.

Variance Analysis:

|  | S.C.E | DDL | C.M. | TEST F | PROBA |
| --- | --- | --- | --- | --- | --- |
| VarTOTAL | 28367.288735 | 9 | 3151.920971 |  |  |
| Var. FACTOR 1 | 26750.325501 | 4 | 6687.581375 | 25.584440 | 0.006094 |
| Var. BLOCKS | 571.393143 | 1 | 571.393143 | 2.185958 | 0.212694 |
| VAR. RESIDUAL 1 | 1045.570091 | 4 | 261.392523 |  |  |

Newman-Keuls Test, 5% Threshold

| Modality | Mean | Homogeneous groups |
| --- | --- | --- |
| Batch 5 | 59.842520 | A |
| Batch 1: NANCO | −51.968504 | B |
| Batch 4 | −62.204724 | B |
| Batch 3 | −64.566929 | B |
| Batch 2 | −86.614173 | B |

Conclusions:

The nematicidal capability linked to this resistance is again confirmed by the test which has been carried out.

The genotype F4.HCR10.M which is resistant to *Heterodera carotae*, with a nematicidal capability of the order of 80% after 4 to 6 months of cultivation, means that an effect comparable to a chemical treatment can be obtained (with an efficiency of 80-90%).

This genotype had already demonstrated the best nematicidal capability in the preceding test; seeds obtained by multiplication of this genotype have been deposited with the NCIMB under the number NCIMB 42351.

LIST OF REFERENCES

Murashige T and Skoog F (1962) A revised medium for rapid growth and bioassays with tobacco tissue cultures. Physiol Plant 15(3): 473-497.

Steward, F. C., Mapes, M. O., and Smith, J. (1958). Growth and organized development of cultured cells. I, II & III. Growth and division of freely suspended cells. Am. J. Bot. 45

The invention claimed is:

1. A method for reducing the population of *Heterodera carotae* nematodes in a cultivation medium infested with such nematodes, comprising cultivating *Daucus carota* plants which do not belong to the sub-species of cultivated *Daucus carota* subsp. *sativus* carrots in such medium so that said plants have a nematicidal effect on said nematodes, wherein said plants are grown from seeds deposited under accession number NCIMB 42351.

2. The method according to claim 1, wherein said reduction in the population of nematodes involves a reduction in the number of cysts and/or J2 juveniles.

3. The method according to claim 1, wherein said cultivating is for at least 4 months.

4. The method according to claim 1, wherein the infested cultivation medium is earth or sand in an open field.

5. The method according to claim 1, wherein the level of infestation of the cultivation medium is reduced to less than one J2 female *Heterodera carotae* larva per gram of medium.

6. The method according to claim 1, wherein the population of *Heterodera carotae* nematodes in the cultivation medium is reduced by at least 40%.

7. The method according to claim 1, wherein the number of cysts or female nematodes in the cultivation medium is reduced by at least 50%.

8. The method according to claim 1, wherein said cultivating is carried out at a density of 0.8 to 1.4 million seeds per hectare.

9. A population of *Daucus carota* plants obtained from seeds deposited under the accession number NCIMB 42351, said plants having a nematicidal effect on a population of *Heterodera carotae* nematodes.

10. The population of carrot plants according to claim 9, wherein the nematicidal effect involves (a) a reduction in the number of J2 juveniles, (b) a reduction in the number of cysts, (c) a masculinization of more than 50% of the larvae of the *Heterodera carotae* nematode, or (d) combinations of (a), (b) and (c), after a cultivation period is of at least 3 months.

11. The method of claim 3 wherein said cultivation period is at least 5 months.

12. The method of claim 3 wherein said cultivation period is at least 6 months.

13. The method of claim 6, wherein the population of *Heterodera carotae* nematodes in the cultivation medium is reduced by at least 50%.

14. The method of claim 6, wherein the population of *Heterodera carotae* nematodes in the cultivation medium is reduced by at least 60%.

15. The method of claim 6, wherein the population of *Heterodera carotae* nematodes in the cultivation medium is reduced by at least 75%.

* * * * *